US008278346B2

(12) United States Patent
He et al.

(10) Patent No.: US 8,278,346 B2
(45) Date of Patent: Oct. 2, 2012

(54) DI-TIN FUSED THIOPHENE COMPOUNDS AND POLYMERS AND METHODS OF MAKING

(75) Inventors: Mingqian He, Horseheads, NY (US); Weijun Niu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 230 days.

(21) Appl. No.: 12/851,998

(22) Filed: Aug. 6, 2010

(65) Prior Publication Data

US 2012/0035375 A1    Feb. 9, 2012

(51) Int. Cl.
*A61K 31/381* (2006.01)
*C07D 495/22* (2006.01)

(52) U.S. Cl. .......................................... 514/443; 549/3
(58) Field of Classification Search .................. 514/443; 549/3

See application file for complete search history.

(56) References Cited

U.S. PATENT DOCUMENTS

| 6,403,809 B1 | 6/2002 | Holmes et al. .................. 549/41 |
| 2007/0112171 A1 | 5/2007 | Li et al. ......................... 528/373 |

FOREIGN PATENT DOCUMENTS

| EP | 1 477 504 | 11/2004 |
| WO | 2005/111045 | 11/2005 |
| WO | 2008/106019 | 9/2008 |
| WO | 2009/101823 | 8/2009 |
| WO | 2009/101914 | 8/2009 |

OTHER PUBLICATIONS

Biniek, L., et al., A [3,2-b]Thienothiophene-alt-benzothiadiazole Copolymer for Photovoltaic Applications: Design, Synthesis, Material Characterization and Device Performance. *J. Materials Chem.*, (2009), 19(28), 4946-4951.
Fong, H. et al., Tetrathienoacene Copolymers As High Mobility, Soluble Organic Semiconductors, *J. Am. Chem. Soc.*, (2008), 130(40), 13202-13203).
He, M., et al., Alkylsubstituted Thienothiophene Semiconducting Materials: Structure-Property Relationships, *J. Am. Chem. Soc.*,(2009), 131(33), 11930-11938.
Landman, M., et al., Synthesis of Iron Thienyl Complexes. *Inorganica Chimica Acta*, (2005), 358(9), 2602-2608 (Abstract).
Lee, J-Y, et al., Low Band-Gap Polymers Based on Quinoxaline Derivatives and Fused Thiophene as Donor Materials for High Efficiency Bulk-Heterojunction Photovoltaic Cells, *J. Materials Chem.* (2009), 19(28), 4938-4945, Scheme 4, *Infra.*).
Li, Jun et al., High-Performance Thin-Film Transistors from Solution-Processed Dithienothiophene polymer Semiconductor Nanoparticles. *Chemistry of Materials* (2008), 20(6), 2057-2059.
Li, Y., et al., Poly(2,5-bis(2-thienyl)-3,6-dialkylthienol[3,2-b]thiophene)s—High-Mobility Semiconductors for Thin-Film Transistors. *Advanced Materials* (Weinheim, Germany) (2006), 18(22), 3029-3032.
Liang, F., et al., Design and Synthesis of Alternating Regioregular Oligothiophenes/Benzothiadiazole Copolymers for Organic Solar Cells, *Macromolecules* (Washington, DC, U.S.) (2009), 42(16), 6107-6114.
McCulloch, I., et al., Liquid-Crystalline Semiconducting Polymers with High Charge-Carrier Mobility. *Nature Materials* (2006), 5(4), 328-333.
San, M., et al., Dialkyl-Substituted Thieno[3,2-b]thiophene-Based Polymers Containing 2,2'-Bithiophene, Thieno[3,2-b]thiophene, and Ethynylene Spacers,*Macromolecules* (Washington, DC, US) (2007), 40(26), 9233-9237.
Sato, M.-A., et al., Oxidized States of Methoxy- and Hexyl-Oligothiophenes with Ferrocenyl Groups. *Synthetic Metals* (2007), 157(16-17), 619-626 (Abstract).
Sato, M., et al., Synthesis and Redox Property of the Binuclear Pt(II) Complexes Bridged by Thieno[3,2-b]thiophenes. *J. Organometallic Chem.*, (2002), 654(1-2), 56-65.
Zhan, X., et al., A High-Mobility Electron-Transport Polymer with Broad Absorption and Its Use in Field-Effect Transistors and All-Polymer Solar Cells. *J. Am. Chem. Soc.*, (2007), 129(23), 7246-7247.
U.S. Appl. No. 12/473,652, filed May 28, 2009, He et al.
Okamato, et al., "General Snythesis of Extended Fused Oligothiophenes Consisting of an Even Number of Thiophene Rings", Chemistry—A European Journal, vol. 13, No. 2, (2006), pp. 548-556.
Rieger, et al., "Tetrathiallexacene as Building Block for Solution-Processable Semiconducting Polymers: Exploring the Monomer Size Limit", Macromolecules, vol. 43, No. 15, (2010), pp. 6264-6267.
Fong, et al., "Tetrathienoacene Copolymers as High Mobility, Soluable Organic Semiconductors", JACS Communications, vol. 130, (2008), pp. 13202-13203.
He, et al., "Importance of C2 Symmetry for the Device Performance of a Newly Synthesized Family of Fused-Ring Thiophenes", Chemistry of Materials, vol. 22, No. 9, (2010), pp. 2770-2779.
He, et al., "Alkylsubstituted Thienothiophene Semiconducting Materials: Structure-Property Relationship", JACS, vol. 131, (2009), pp. 11930-11938.

*Primary Examiner* — Taofiq A Solola
(74) *Attorney, Agent, or Firm* — John L. Haack

(57) ABSTRACT

Di-tin fused thiophene (FT) compounds, FT polymers, such as of the formula -{-(FTx)-(Ar)$_m$-}$_n$-, FT polymer containing articles or devices, and methods for making and using the FT compounds and polymers thereof of the formulas, as defined herein.

16 Claims, No Drawings

DI-TIN FUSED THIOPHENE COMPOUNDS AND POLYMERS AND METHODS OF MAKING

The entire disclosure of any publication, patent, or patent document mentioned herein is incorporated by reference.

BACKGROUND

The disclosure generally relates to fused thiophene compounds, polymers, compositions, articles, and to methods for making and using the thiophene compositions.

SUMMARY

The disclosure provides di-tin fused thiophene (FT) compounds and FT polymers that can be used, for example, for electronic applications, such as light emitting devices and semiconductor devices, and methods of making and using the fused thiophene products.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"FTx" refers to fused thiophene where x is an integer indicating the number of fused thiophene ring or cycle units fused into a single core unit, for example, a FT4 has four fused rings in the core unit, a FT5 has five fused rings in the core unit, a FT6 has six fused rings in the core unit, and like higher designations in the core unit.

"Unit," "polymerizable unit," or like terms in the context of the disclosed fused thiophene polymers or copolymers refer to the number of different core units and like other conjugated units within a discrete repeat segment (n) of a polymer or copolymer, see for example the core fused thiophene unit -(FTx)-, the aryl or heteroaryl —(Ar)$_m$—, and combinations thereof, such as -{-(FTx)-(Ar)$_m$-}-. A repeat unit can have one or more like core units and one or more additional conjugated units within a discrete repeat segment of a polymer.

"Hydrocarbon," "hydrocarbyl," "hydrocarbylene," "hydrocarbyloxy," and like terms refer to monovalent such as —R, or divalent —R— moieties, and can include, for example, alkyl hydrocarbons, aromatic or aryl hydrocarbons, alkyl substituted aryl hydrocarbons, alkoxy substituted aryl hydrocarbons, heteroalkyl hydrocarbons, heteroaromatic or heteroaryl hydrocarbons, alkyl substituted heteroaryl hydrocarbons, alkoxy substituted heteroaryl hydrocarbons, and like hydrocarbon moieties, and as illustrated herein.

"Alkyl" includes linear alkyls, branched alkyls, and cycloalkyls. "Substituted alkyl" or "optionally substituted alkyl" refers to an alkyl substituent, which can include, for example, a linear alkyl, a branched alkyl, or a cycloalkyl, having from 1 to 4 optional substituents selected from, for example, hydroxyl (—OH), halogen, amino (—NH$_2$ or —NR$_2$), nitro (—NO$_2$), acyl (—C(=O)R), alkylsulfonyl (—S(=O)$_2$R), alkoxy (—OR), and like substituents, where R of the optional substituent can be a hydrocarbyl, aryl, Het, or like moieties, such as a monovalent alkyl or a divalent alkylene having from 1 to about 10 carbon atoms. For example, a hydroxy substituted alkyl, can be a 2-hydroxy substituted propylene of the formula —CH$_2$—CH(OH)—CH$_2$—, an alkoxy substituted alkyl, can be a 2-methoxy substituted ethyl of the formula —CH$_2$—CH$_2$—O—CH$_3$, an amino substituted alkyl, can be a 1-dialkylamino substituted ethyl of the formula —CH(NR$_2$)—CH$_3$, an oligo-(oxyalkylene), poly-(oxyalkylene), or poly-(alkylene oxide) substituted alkyl, can be, for example, of the partial formula —(R—O)$_x$—, where x can be, for example, from 1 to about 50, and from 1 to about 20, and like substituted oxyalkylene substituents, such as of the formula —(CR$^5$—CHR$^5$—O)$_x$— where R$^5$ is hydrogen or a substituted or unsubstituted (C$_{1-8}$) hydrocarbyl such as alkyl, and x is an integer of from 1 to about 50.

"Aryl" includes a mono- or divalent-phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents. Aryl (Ar) includes substituted or unsubstituted, heteroaryls or heterocyclics.

"Het" includes a four-(4), five-(5), six-(6), or seven-(7) membered saturated or unsaturated heterocyclic ring having 1, 2, 3, or 4 heteroatoms selected from the group consisting of oxy, thio, sulfinyl, sulfonyl, selenium, tellurium, and nitrogen, which ring is optionally fused to a benzene ring. Het also includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, (C$_{1-4}$)alkyl, phenyl, or benzyl, and a radical of an ortho-fused bicyclic heterocycle of about eight to ten ring atoms derived therefrom, particularly a benzo-derivative or one derived by fusing a propylene, trimethylene, or tetramethylene diradical thereto. A particularly useful Aryl (Ar) includes substituted or unsubstituted, divalent thiophene.

In embodiments, halo or halide includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

The carbon atom content of various hydrocarbon-containing (i.e., hydrocarbyl) moieties can alternatively be indicated by a prefix designating a lower and upper number of carbon atoms in the moiety, i.e., the prefix C$_{i-j}$ indicates a moiety of the integer "i" to the integer "j" carbon atoms, inclusive. Thus, for example, C$_1$ to C$_8$ alkyl, (C$_1$-C$_8$)alkyl, or C$_{1-8}$alkyl refers to an alkyl of one to eight carbon atoms, inclusive, and hydrocarbyloxy such as (C$_1$-C$_8$)alkoxy or C$_{1-8}$alkoxy refers to an alkoxy radical (—OR) having an alkyl group of one to eight carbon atoms, inclusive.

Specifically, C$_{1-8}$alkyl can be, for example, methyl, ethyl, propyl, isopropyl, butyl, iso-butyl, sec-butyl, tert-butyl, pentyl, 3-pentyl, hexyl, heptyl, or octyl; (C$_{3-12}$)cycloalkyl can be cyclopropyl, cyclobutyl, cyclopentyl, cyclohexyl, cycloheptyl, cyclooctyl, etc., including bicyclic, tricyclic, or multicyclic substituents, and like substituents.

A specific "hydrocarbyl" can be, for example, (C$_{1-24}$)hydrocarbyl, including all intermediate chain lengths and values.

C$_{1-8}$alkoxy can be, for example, methoxy, ethoxy, propoxy, isopropoxy, butoxy, iso-butoxy, sec-butoxy, pentoxy, 3-pentoxy, hexyloxy, 1-methylhexyloxy, heptyloxy, octyloxy, and like substituents.

H—C(=O)(C$_{3-7}$)alkyl- or —(C$_{2-7}$)alkanoyl can be, for example, acetyl, propanoyl, butanoyl, pentanoyl, 4-methylpentanoyl, hexanoyl, or heptanoyl. Aryl (Ar) can be, for example, phenyl, naphthyl, anthracenyl, phenanthrenyl, fluorenyl, tetrahydronaphthyl, or indanyl. Het can be, for example, pyrrolidinyl, piperidinyl, morpholinyl, thiomorpholinyl, or heteroaryl. Heteroaryl can be, for example, furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), or quinolyl (or its N-oxide).

A specific value for Het includes a five-(5), six-(6), or seven-(7) membered saturated or unsaturated ring containing 1, 2, 3, or 4 heteroatoms, for example, non-peroxide oxy, thio, sulfinyl, sulfonyl, selenium, tellurium, and nitrogen; and a radical of an ortho-fused bicyclic heterocycle of about eight to twelve ring atoms derived therefrom, particularly a benzo-derivative or one derived by fusing a propylene, trimethylene, tetramethylene, or another monocyclic Het diradical thereto.

Other conditions suitable for formation and modification of the compounds, oligomers, polymers, composites or like products of the disclosure, from a variety of starting materials or intermediates, as disclosed and illustrated herein, are available. For example, see Feiser and Feiser, "Reagents for Organic Synthesis", Vol. 1, et seq., 1967; March, J. "Advanced Organic Chemistry," John Wiley & Sons, 4$^{th}$ ed. 1992; House, H. O., "Modem Synthetic Reactions," 2$^{nd}$ ed., W. A. Benjamin, New York, 1972; and Larock, R. C., "Comprehensive Organic Transformations," 2$^{nd}$ ed., 1999, Wiley-VCH Publishers, New York. The starting materials employed in the preparative methods described herein are, for example, commercially available, have been reported in the scientific literature, or can be prepared from readily available starting materials using procedures known in the field or provided in the working examples. It may be desirable to optionally use a protecting group during all or portions of the above described or alternative preparative procedures. Such protecting groups and methods for their introduction and removal are known in the art. See Greene, T. W.; Wutz, P. G. M. "Protecting Groups In Organic Synthesis," 2$^{nd}$ ed., 1991, New York, John Wiley & Sons, Inc.

"Include," "includes," or like terms means encompassing but not limited to, that is, inclusive and not exclusive.

"Monomer," "mer," or like terms refer to a compound that can be (or has already been) covalently combined or linked with other monomers of like or different structure to form homogenous (homopolymers) or heterogeneous (e.g., copolymers, terpolymers, and like heteropolymers) chains of the target polymer. "Polymer" or like terms includes copolymers. Suitable monomers as disclosed and illustrated herein can include, for example, low molecular weight polymerizable compounds, such as from about 50 to about 200 Daltons, and higher molecular weight compounds, such as from about 200 to about 10,000 Daltons, including divalent or bifunctionally reactive compounds as disclosed herein, such as di-tin fused thiophene compounds, di-halogen thiophene compounds, di-halogen oligo-thiophene compounds, and like compounds.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, composites, concentrates or use formulations; through inadvertent error in these procedures; through differences in the manufacture, source, or purity of starting materials or ingredients used to carry out the methods; expressing measured polymer number average or weight average molecular weight properties, and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto include equivalents of these "about" quantities.

"Consisting essentially of" in embodiments refers, for example, to a compound, to a polymer or copolymer composition, to a method of making or using the compound, the polymer, the copolymer, a formulation, or composition, and articles, devices, or any apparatus of the disclosure, and can include the components or steps listed in the claim, plus other components or steps that do not materially affect the basic and novel properties of the compositions, articles, apparatus, or methods of making and use of the disclosure, such as particular reactants, particular additives or ingredients, a particular agent, a particular monomer, co-monomer, or condition, or like structure, material, or process variable selected. Items that may materially affect the basic properties of the components or steps of the disclosure or that may impart undesirable characteristics to the present disclosure include, for example, premature polymer chain termination, excessive crosslinking, extended or unnecessary exposure of the resulting polymer to excessively high temperatures, and like contrary steps.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, reactants, reagents, ingredients, additives, initiators, metal catalysts, cross linkers, and like aspects, and ranges thereof, are for illustration only; they do not exclude other defined values or other values within defined ranges. The compositions and methods of the disclosure include those having any value or any combination of the values, specific values, more specific values, and preferred values described herein.

In embodiments, the disclosure provides FT compounds, FT polymer compositions, FT and aryl copolymer compositions, FT containing articles, and methods for making and using the FT compounds and the FT polymers.

In embodiments, the disclosure provides an FT compound and a method of making an FT compound as defined herein.

In embodiments, the disclosure provides an FT polymeric or FT copolymeric composition, and FT articles thereof prepared by any of the processes as defined herein.

In embodiments, the disclosure provides a polymer article prepared by one or more of the processes as defined herein.

In embodiments, the disclosure provides an article or device incorporating the polymer, copolymeric, or polymer article as defined herein. The disclosed compositions, articles, and methods can be used to prepare many different electro-optical devices, for example, OLEDs, OFETs, OTFTs, and like devices as disclosed, for example, in *J. Am. Chem. Soc.*, 2008, 130, 13202-13203.

In embodiments, the disclosure provides a compound of the formula (I) or (II):

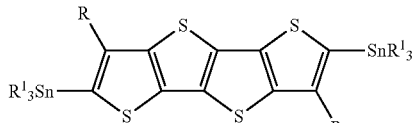

(I)

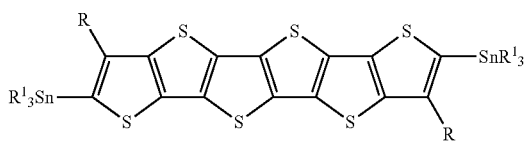

(II)

where each R is independently —H, or a substituted or unsubstituted, $(C_{1-24})$hydrocarbyl;

each $R^1$ is independently —H, or a substituted or unsubstituted, $(C_{1-10})$hydrocarbyl;

or a combination thereof, and a salt thereof.

The R can be, for example, a $C_{10}$ to $C_{18}$ alkyl, and $R^1$ is a $C_1$ to $C_6$ alkyl. The R can be, for example, $C_{17}H_{35}$ and $R^1$ can be, for example, $CH_3$. The di-tin compound $R^1{}_3Sn$-DC17FT4-$SnR^1{}_3$ of the formula (I) where $R^1$ is $CH_3$, has excellent solubility in hexane, toluene, $CH_2Cl_2$, or mixtures thereof, compared to the corresponding di-bromo compound Br-DC17FT4-Br of the formula (V). A specific di-bromo fused thiophene compound of the formula (V) is the diBrDC17FT4 compound 7. A specific di-tin fused thiophene compound of the formula (I) is the di-tin-DC17FT4 compound 2 in Scheme 3 and compound 8 in Scheme 8.

In embodiments, the disclosure provides a method of making a polymer of formula (III) or (IV):

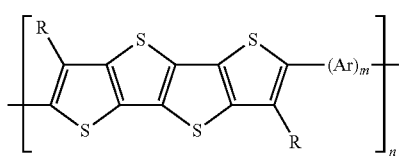

(III)

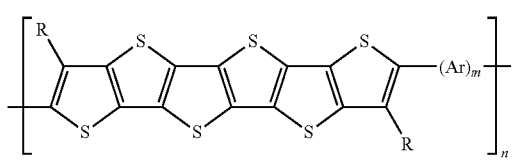

(IV)

comprising:

contacting a dihalogen compound of formula (V) or (VI)

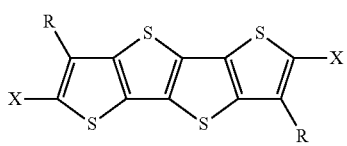

(V)

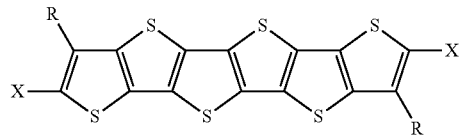

(VI)

and at least two equivalents of an alkyl lithium reagent or an aryl lithium reagent to form the metal-halogen exchange intermediate, and then contacting the intermediate with a trialkylene tin halide compound to form the di-tin compound of formula (I) or (II):

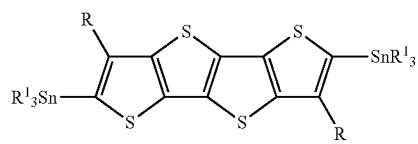

(I)

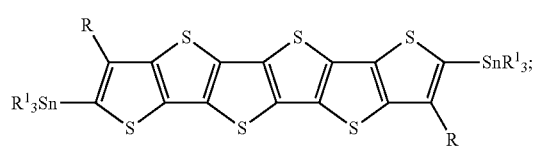

(II)

and contacting the compound of formula (I) or (II) with a dihalogen aryl compound or dihalogen heteroaryl compound of the formula $X-(Ar)_m-X$, and a metal catalyst to form the polymer of the formula (III) or (IV), where m, and n, are independently integers from 1 to about 20, each R is independently —H, or a substituted or unsubstituted, $(C_{1-24})$hydrocarbyl;

each $R^1$ is independently —H, or a substituted or unsubstituted, $(C_{1-10})$hydrocarbyl;

each Ar is independently a substituted or unsubstituted divalent aryl or heteroaryl, and X is halogen, and a salt thereof.

The dihalogen aryl compound or dihalogen heteroaryl compound of the formula $X-(Ar)_m-X$ can be, for example, Br-(thiophene)$_m$-Br and m is 2 to 4. The dihalogen aryl compound or dihalogen heteroaryl compound of the formula $X-(Ar)_m-X$ can be, for example, a Br-{(thiophene)$_a$(beta-alkyl-substituted-thiophene)$_b$}$_m$-Br where the beta-alkyl-substituent R is —$C_{17}H_{35}$, a is 2, b is 2, and m is the sum of aryl or heteroaryl units in the dihalogen monomer. The dihalogen aryl compound or dihalogen heteroaryl compound of the formula $X-(Ar)_m-X$ can be, for example, a Br-{(beta-$C_{17}$-substituted-thiophene) (thiophene)$_2$ (beta-$C_{17}$-substituted-thiophene)}-Br, where a is two (2) (beta-$C_{17}$-substituted-thiophene) groups, b is two (2) (thiophene) groups, and m is 4.

The alkyl lithium reagent or an aryl lithium reagent can be, for example, selected from n-butyl lithium, t-butyl lithium, phenyl lithium, and like reagents, or a combination thereof. The metal-halogen exchange can be, for example, accomplished in refluxing hexane and the alkyl lithium reagent is n-butyl lithium.

In embodiments, the disclosure provides a OTFT device, such as OTFT and like devices, comprising at least one polymer of the formula (III), (IV):

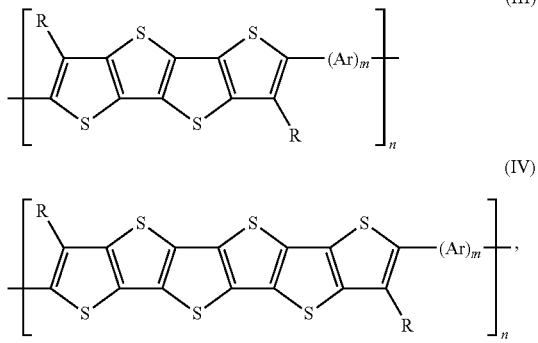

where R, Ar, m, and n are as defined herein, and salts thereof, or a mixture thereof.

The polymer can be, for example, of the formula (III) where R is $C_{17}H_{35}$, Ar is -{(beta-$C_{17}$-substituted-thiophene) (thiophene)$_2$ (beta-$C_{17}$-substituted-thiophene)}-, m is 4, and n is from 5 to 20. The mobility for a OTFT device made from this particular polymer of formula (III) was measured to be about $0.0155$ $cm^2V^{-1}s^{-1}$ and the on/off ratio was about $10^5$.

In the preparative method to form the polymer, a monomer of the general formula M-(FTx)-M can be, for example, where M is an organometallic group together with the FTx a disubstituted fused thiophene is coupling compound, for example, of the formula $R^1{}_3$Sn-(FTx)-Sn$R^1{}_3$ where FTx is, for example, a di($C_{1-24}$)hydrocarbyl substituted, 4- or 6-membered fused thiophene system, using Stille coupling conditions, or like conditions, or combinations thereof, where $R^1$ can independently be a monovalent or divalent ($C_{1-8}$) hydrocarbyl such as alkyl, alkylene, alkyne, including branched and cyclic hydrocarbyls such as cyclo($C_{3-8}$)alkyl, cyclic divalent ($C_{1-8}$)hydrocarbyls or combinations thereof, and like substituents. The di-tin fused thiophene compounds of the formula $R^1{}_3$Sn-(FTx)-Sn$R^1{}_3$ can be prepared by, for example, metal-halogen exchange with a suitable organometallic reagent, such as an alkyl lithium reagent and a dihalogen compound of the formula X-(FTx)-X, where X is halogen, and -(FTx)- can be a divalent fused thiophene moiety of the formula, for example, substituted and unsubstituted -(FT4)- or -(FT6)-cores, and mixtures thereof, or a salt thereof.

Specific dihalogenated compounds of the formula X-(FTx)-X can be, for example, of the formulas Br-DCxFT4-Br and Br-DCxFT6-Br, where FT is the fused thiophene core, and DC is the dialkyl substituents of carbon chain length x attached to the FT core.

In embodiments, the disclosure also provides fused thiophene core compounds and their corresponding polymers having one or more additional mer units included or appended to the core. In embodiments, the additional appended unit or units can participate in polymerization and chain extension. The resulting product can be a polymer having a repeat segment (n) including, for example, at least one core unit (C) having four or more fused thiophene rings, and at least one —(Ar)— unit. In embodiments, the resulting product can be a polymer having a repeat segment including, for example, a single fused thiophene core unit -(FTx)-, at least two covalently bonded —(Ar)— units, for example —(Ar)$_2$—. In embodiments, the disclosure provides a method for preparing polymers and block copolymers having chain segments containing, for example, from about 4 to about 10 fused thiophene units, and from about 2 to about 10 contiguous Ar units. In embodiments, the disclosure provides a method for preparing fused thiophene containing polymers and block copolymers using, for example, Stille coupling reactions.

In embodiments, the disclosure provides di-tin β-, β'-alkyl substituted fused thiophene compounds that have improved solubility in common organic solvents compared to di-bromo β-, β'-substituted fused thiophene compounds. The excellent solubility property makes these materials and their conjugated polymer products suitable for use in solution processing of organic electronics, particularly for printing applications (see PCT Appl. PCT/US2009/001965 filed Mar. 30, 2009, U.S. Ser. No. provisional patent application No. 61/072,468, assigned to Corning, Inc., filed Mar. 31, 2008, entitled "Fused Thiophenes and Methods for Making and Using Same"; Fong, H. et al., Tetrathienoacene Copolymers As High Mobility, Soluble Organic Semiconductors, *J. Am. Chem. Soc.*, (2008), 130(40), 13202-13203). The disclosed fused thiophene compounds and polymers also exhibit excellent thermal stability and air stability compared to, for example, pentacene, which rapidly decomposes in solution and in the presence of air.

In embodiments, the compounds of the disclosure provide advantages, including for example:

the simplicity or ease with which one can synthetically manipulate or systematically change one or more of the mers or units in the polymer to produce new polymer structures having highly regular or repeat conjugated structure;

the disclosed polymer preparative methods provide additional flexibility or capability to specify the regio-regularity of the polymer structures; and the disclosed methods can be used to make known polymers (see for example commonly owned and assigned copending application U.S. Ser. No. 61/072,468,) more efficiently, such as with fewer steps and fewer reagents.

Based upon other known and related compounds and polymers, the disclosed compounds and polymers are expected to have excellent organic semiconductor properties, such as increased thermal stability and oxygen stability, and increased ease of manufacture based on increased solubility and increased synthetic efficiency, such as fewer steps.

Highly conjugated polymers have been the recent focus of academic or industrial research, mainly due to their interesting electronic and optoelectronic properties. They have a variety of applications including organic thin film transistors (OTFTs), organic light-emitting diodes (OLEDs) and electro-optic (EO) applications. Several of them are soluble polymeric semiconductors having a repeat unit of two to seven-membered fused thiophene rings which have been used as high performance field-effect transistors (see for example, He, M., Fused Thiophene Monomers, Oligomers and Polymers for use in Electronic Devices. PCT Int. Appl. (2008), WO2008/106019A2 (PCT/US2008/002033); Fong, H. H., et al., supra.; He, M., et al., Alkylsubstituted Thienothiophene Semiconducting Materials: Structure-Property Relationships, *J. Am. Chem. Soc.*, (2009), 131(33), 11930-11938; Li, Jun et al., High-Performance Thin-Film Transistors from Solution-Processed Dithienothiophene polymer Semiconductor Nanoparticles. *Chemistry of Materials* (2008), 20(6), 2057-2059; Zhan, X., et al., A High-Mobility Electron-Transport Polymer with Broad Absorption and Its Use in Field-Effect Transistors and All-Polymer Solar Cells. *J. Am. Chem. Soc.*, (2007), 129(23), 7246-7247; Heeney, M. et al., Mono-, Oligo- and Polythieno[3,2-b]thiophenes Use as Semiconductors or Charge Transport Materials. PCT Int. Appl. (2005), 47 pp. WO 2005111045 (PCT/EP2005/004271); McCulloch, I., et al., Liquid-Crystalline Semiconducting Polymers with High Charge-Carrier Mobility. *Nature Materials* (2006), 5(4), 328-333; Biniek, L., et al., A [3,2-b]Thienothiophene-alt-benzothiadiazole Copolymer for Photovoltaic Applications: Design, Synthesis, Material Characterization and Device Performance. *J Materials Chem.*, (2009), 19(28), 4946-4951; Li, Y., et al., Poly(2,5-bis(2-thienyl)-3,6-dialkylthienol[3,2-b]thiophene)s- High-Mobility Semiconductors for Thin-Film Transistors. *Advanced Materials* (Weinheim, Germany) (2006), 18(22), 3029-3032; Li, Y., et al., Polymer Having Thieno[3,2-b]thiophene Moieties, U.S. Pat. Appl. Publ. (2007), 2007/0112171A1; Liang, F., et al., Design and Synthesis of Alternating Regioregular Oligothiophenes/Benzothiadiazole Copolymers for Organic Solar Cells, *Macromolecules* (Washington, D.C., U.S.) (2009), 42(16), 6107-6114.

The fused thiophene polymers disclosed in commonly owned and assigned WO2008/106019 (supra.) were synthesized by Stille coupling between a dibromo fused thiophene monomer and a di-tin non-fused aromatic monomer (or a vinyl di-tin monomer) (Scheme 1). Although the synthesis of a dibromo fused thiophene monomer from the parent fused thiophene is not difficult, the purification of certain highly conjugated non-fused aromatic di-tin monomers (or vinyl compounds) is not trivial due to their easy decomposition. For example, in our research for a polymer having greater solubility while maintaining the high device performance of our reported β-, β'-alkyl substituted four-membered fused thiophene polymer (see Fong, H. H., supra.), we conceived a synthesis of β-, β'-alkyl substituted four-membered fused thiophene polymer having a repeat unit with $C_2$ symmetry by the reaction of a fused thiophene dibromo monomer and the highly conjugated non-fused aromatic β-, β'-alkyl substituted di-tin monomer, compound 1 (Scheme 2). It was found that this highly conjugated non-fused aromatic di-tin monomer 1 decomposed during recrystallization in the organic solvents tried.

Bithiophene and the more conjugated quaterthiophene are commercially available.

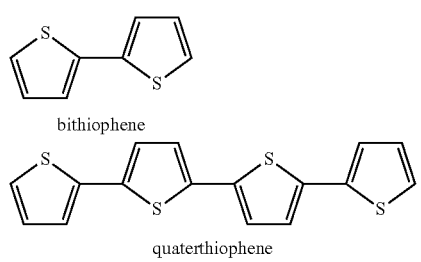

bithiophene quaterthiophene

A 2010 SciFinder search produced 128 papers on the di-tin compounds of bithiophene, whereas only one communication reported a synthesis of a di-tin compound of quaterthiophene but without NMR support (see Kang, B. S., et al., Wavelength Tuning of Light-Emitting Polyarenes via an m-Phenylene Interrupting Block: Band-Gap Adjustment of Thiophene-Based Conjugated Polymers, *Chem. Comm.* (Cambridge, UK) (1996), (10), 1167-1168). This suggests the synthesis and purification of this di-tin compound of quaterthiophene is potentially challenging. A di-tin compound of 3,3'-dihexyl quaterthiophene has been prepared and the $^1$H NMR of the crude product was reported (see Karakawa, M., et al., Organic Semiconductor Polymer, Organic Thin Film Using the Same, and Organic Thin Film Device, WO 2009101914; Ie, Y., et al., Branched Compounds, Organic Thin Films Using the Same, and Organic Thin Film Device. WO 2009101823; Ie, Y., et al., Dendritic Oligothiophene Bearing Perylene bis(dicarboximide) Groups as an Active Material for Photovoltaic Device. *Chem. Comm.* (Cambridge, UK) (2009), (10), 1213-1215; Sato, M.-A., et al., Oxidized States of Methoxy- and Hexyl-Oligothiophenes with Ferrocenyl Groups. *Synthetic Metals* (2007), 157(16-17), 619-626). However, Sato's di-tin compound of 3,3'-dihexyl quaterthiophene was used without any purification for oligomer synthesis, presumably due to its difficult purification.

In embodiments, the present disclosure overcomes the purification issue by reacting a four-membered fused thiophene di-tin monomer 2 and a highly conjugated non-fused aromatic dibromo monomer 3 to obtain the polymer 4 (Scheme 3). Based on an apparent higher HOMO-LUMO gap, it is believed that this four-membered fused thiophene di-tin monomer 2 (Scheme 3) should be much more thermally stable than the highly conjugated non-fused aromatic di-tin monomer 1 (a quaterthiophene derivative in Scheme 2). Indeed, we were able to obtain this fused thiophene di-tin monomer 2 in excellent purity (>95%) after recrystallization from diethyl ether. The literature reports three examples of β-, β'-alkyl substituted fused thiophene di-tin compounds consisting of two-membered ring fused thiophene (FT2) di-tin compounds (see Sato, M., et al., Synthesis and Redox Property of the Binuclear Pt(II) Complexes Bridged by Thieno[3,2-b]thiophenes. *J. Organometallic Chem.*, (2002), 654(1-2), 56-65; Landman, M., et al., Synthesis of Iron Thienyl Complexes. *Inorganica Chimica Acta*, (2005), 358(9), 2602-2608; and Lee, J-Y, et al., Low Band-Gap Polymers Based on Quinoxaline Derivatives and Fused Thiophene as Donor Materials for High Efficiency Bulk-Heterojunction Photovoltaic Cells, *J. Materials Chem.* (2009), 19(28), 4938-4945, Scheme 4, infra.).

Several di-tin compounds of non-substituted fused thiophenes with either two- or three-ring fused rings have been used as a monomer for conjugated polymer synthesis (see Li, et al., Zhan, et al., Heeney, et al., McCulloch, et al., Biniek, et al., Li, et al., and Liang, et al., supra.). One example was the synthesis of β-, β'-alkyl substituted fused thiophene polymers accomplished by Stille coupling using a fused thiophene di-tin monomer and an aromatic dibromo monomer (or a dibromo vinyl compound) (see Lee, et al., ibid. and Scheme 4 below).

In embodiments, the disclosure provides methods for preparing di-tin β-, β'-alkyl substituted fused thiophene monomers and the fused thiophene di-tin monomers (Scheme 5). The disclosure also provides an alternative preparative method to form conjugated polymers of β, β'-alkyl substituted fused thiophenes. The fused thiophene copolymers can be synthesized by the Stille coupling using β-, β'-alkyl substituted fused thiophene di-tin monomer and a dibromo aromatic monomer (or a dibromo vinyl monomer) (Scheme 6).

In embodiments, the present disclosure provides general methods to synthesize di-tin β-, β'-alkyl substituted fused thiophene monomers (Scheme 5), and polymers or copolymers of these di-tin fused thiophene monomers. Experimental examples demonstrated that these fused thiophene polymers can be synthesized by the Stille coupling using a β-, β'-alkyl substituted fused thiophene di-tin monomer and an aromatic dibromo monomer (or a vinyl compound) (Scheme 6). These fused thiophene monomers can have from four-fused rings to seven-fused thiophene rings. In embodiments, the disclosed monomers and preparative methods are especially useful for preparing fused thiophene monomers, and polymers, or copolymers thereof having four-membered fused ring (FT4) or six-membered fused ring (FT6) core ring systems.

In embodiments, polymer 4, having unique solubility characteristics, was prepared by the disclosed method. The disclosure also demonstrated that these fused thiophene di-tin monomers can be used to synthesize α-, α'-aromatic ring substituted, β-, β'-alkyl substituted fused thiophenes (see commonly owned and assigned copending patent application U.S. Ser. No. 12/473,652, to He, et al., entitled Fused Thiophenes, Articles, and Methods Thereof), and α-, α'-aromatic ring substituted, β-, β'-alkyl substituted three-membered (or two-membered) fused thiophenes mentioned in the literature (see San, M., et al., Dialkyl-Substituted Thieno[3,2-b]thiophene-Based Polymers Containing 2,2'-Bithiophene, Thieno[3,2-b]thiophene, and Ethynylene Spacers, *Macromolecules* (Washington, D.C., US) (2007), 40(26), 9233-9237; Frey, J., et al., Improved Synthesis of Dithieno[3,2-b:2',3'-d]thiophene (DTT) and Derivatives for Cross Coupling, *Chem. Comm.* (Cambridge, UK) (2002), (20), 2424-2425. (Scheme 7).

In embodiments, the disclosure further improves upon novel organic electronic materials and methods of making. The new di-tin β-, β'-alkyl substituted fused thiophene monomers were prepared from known materials (Scheme 5). These new di-tin monomers are a reactant in an alternative route to high performance β-, β'-alkyl substituted fused thiophene polymers (FT4-FT7 polymers) (Scheme 6).

The disclosed method provides an alternative preparative route to certain β-, β'-alkyl substituted two-membered fused thiophene polymers (FT2 polymers) (Scheme 6). The prior art preparative method used Stille coupling to prepare these polymers by reacting a fused thiophene dibromo monomer with a non-fused aromatic di-tin monomer (or a vinyl compound).

The present disclosure's alternative method prepares these polymers by the Stille coupling between a β-, β'-alkyl substituted fused thiophene di-tin monomer and a non-fused aromatic dibromo monomer (or a vinyl dibromo monomer) (Scheme 6).

Advantages of the present preparative methods include, for example, the relatively straightforward path to a variety of new polymers and copolymers, especially those polymers having a core member having four or six fused thiophenes. The di-tin fused thiophene monomer compounds are convenient to prepare because of their high crystallinity and solubility characteristics, and the di-tin fused thiophene monomer compounds possess greater solubility compared to the above-mentioned prior art dibromo monomer compounds.

The solid state nature of β-, β'-alkyl substituted fused thiophene di-tin monomers (for example, di-tin compound 2 in Scheme 3), allows them to be purified by solvent recrystallization. This permits the use of a wide variety of commercially available dihalo, such as dibromo, non-fused aromatic co-monomers or dihalo vinyl co-monomers for polymerization.

In embodiments, polymer materials of the disclosure can have a repeat unit with $C_2$ symmetry. The more soluble polymer of β-, β'-alkyl substituted four-membered fused thiophene (polymer 4 in Scheme 3) can be synthesized by the reaction of a fused thiophene di-tin monomer (2) and the highly conjugated non-fused aromatic dibromo monomer (3) (Scheme 3). This approach avoids using the unstable di-tin compound 1.

It was found that the fused thiophene (FT4) di-tin monomer compound 2 (Scheme 3) can be synthesized under certain disclosed conditions and purified by recrystallization to an off-white crystalline solid in good yield (74%) whereas the conjugated non-fused aromatic di-tin monomer with the same number of aromatic rings (compound 1 in Scheme 2) could only be purified as an oily product in about 85% purity through distillation or low temperature recrystallization. Use of the fused thiophene (FT4) di-tin monomer compound 2 instead of the conjugated non-fused aromatic di-tin monomer having the four un-fused thiophene rings (compound 1 in Scheme 2) is a surprising and unexpected processing advantage. The disclosed di-tin fused thiophene (FT4) compounds were highly crystalline and readily purified by differential solvent recrystallization. In contrast, the FT2 di-tin compounds were waxy solid compounds which were difficult to purify and were used without any purification.

DC17FT4 di-tin compound 2 (Scheme 3) is also much more soluble than DC17FT4 dibromo compound 7 (Scheme 8) in many organic solvents (Table 2). For example, the DC17FT4 di-tin compound is freely soluble in both diethyl ether and hexane at room temperature, whereas the DC17FT4 dibromo compound is practically insoluble in either or both diethyl ether and hexane at room temperature. This solubility property can be very useful in the scale-up synthesis of the high performance polymer (P2TDC17FT4) of the formula:

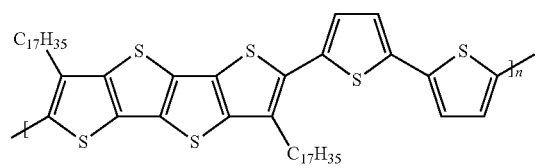

The disclosed preparative method can be extended to any fused aromatic di-tin monomer. The disclosed copolymer preparative method can also be extended to the synthesis of conjugated polymers of any fused aromatics.

Scheme 1. Prior Art Route to Fused Thiophene Polymers.

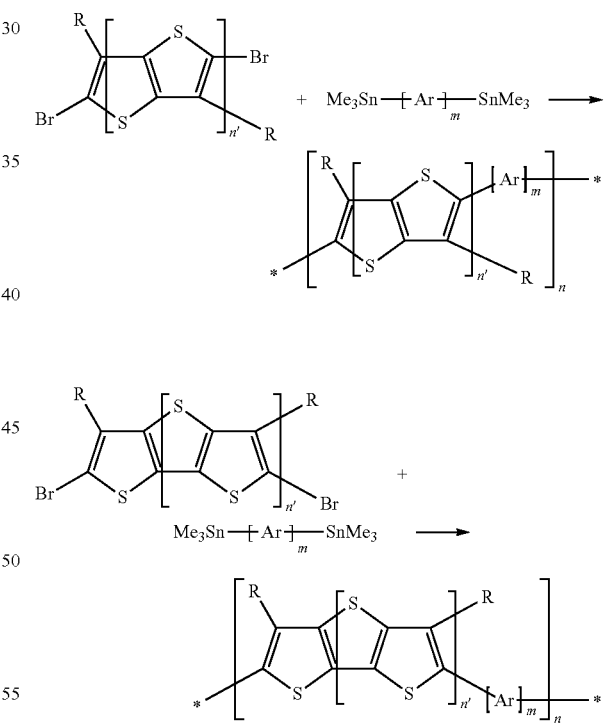

Scheme 2 illustrates an example for preparing a β-, β'-alkyl substituted four-membered fused thiophene (FT4) copolymer by the reaction of the FT4 fused thiophene dibromo monomer and a highly conjugated non-fused aromatic di-tin quaterthiophene monomer 1 in the presence of a suitable Pd metal or complex, or like catalyst. The metal catalyst can be, for example, $Pd(PPh_3)_4$, or like agents, such as based on Pt, Ni, or like metals. The di-tin monomer 1 used was an oily liquid about 85% pure.

Scheme 2.

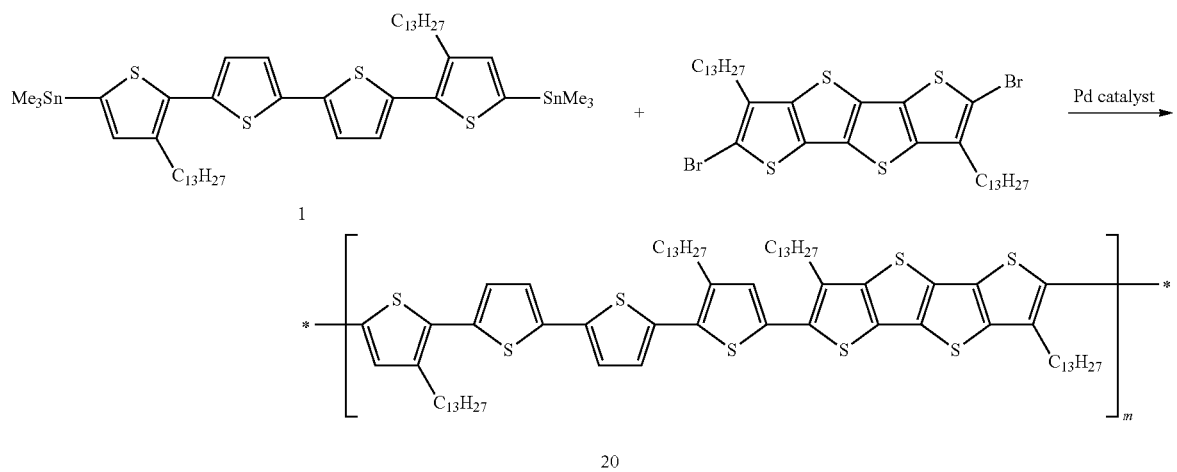

Scheme 3 generally illustrates the inventive alternative and superior method for preparing β-, β'-alkyl substituted four-membered fused thiophene copolymers, such as of the formula 4, that can be achieved by reacting the fused thiophene (FT4) di-tin monomer 2 with the highly conjugated non-fused aromatic dibromo quaterthiophene monomer 3 in the presence of a suitable Pd or like catalyst.

Scheme 3.

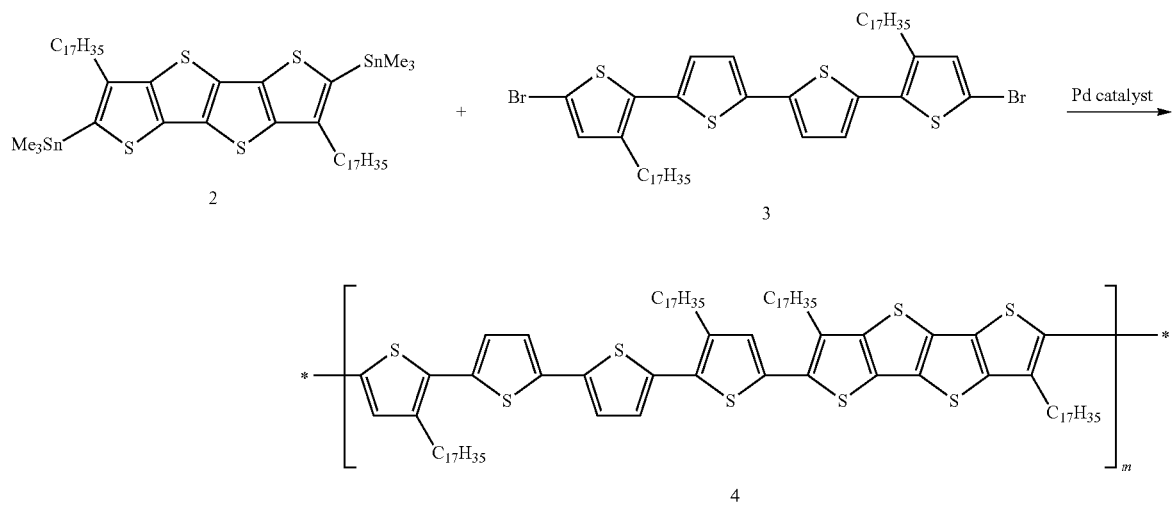

Scheme 4 illustrates a previously described polymerization method (see Lee, J-Y, et al., supra.) where a β-, β'-alkyl substituted fused thiophene polymer was prepared be reacting a fused thiophene di-tin monomer with a dibromo monomer.

Scheme 4.

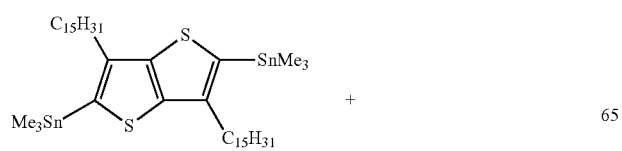

-continued

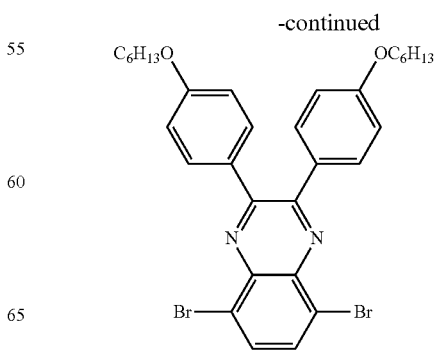

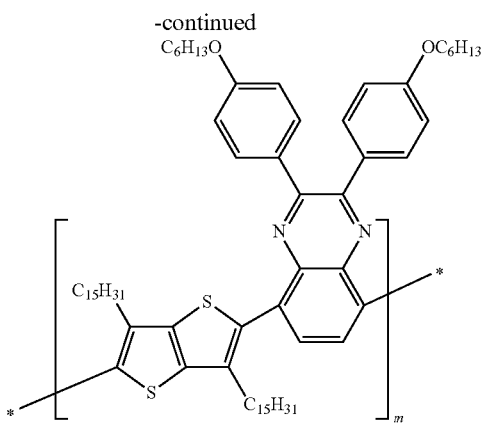

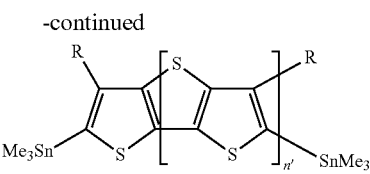

Scheme 5 shows two exemplary routes to β-, β'-alkyl substituted fused thiophene di-tin monomers by, for example, metal-halogen exchange of a dibromo di-R substituted FT compound with an organo-lithium reagent or like reagent followed by reaction with the tin reagent, or reaction of the non-halogenated di-R substituted FT compound with an organo-lithium reagent or like reagent followed by reaction with the tin reagent, where R is alkyl and n' is an integer from 1 to 3.

Scheme 6 shows an alternative preparative route to β-, β'-alkyl substituted fused thiophene polymers by reaction of a fused thiophene di-tin monomer with a non-fused aromatic dibromo monomer of the formula Br—(Ar)$_m$—Br, where, for example, R is alkyl, m can be an integer of from 1 to 10, n' can be an integer of from 1 to 3, and n can be an integer of from 1 to 1,000, including intermediate values and ranges.

Scheme 5.

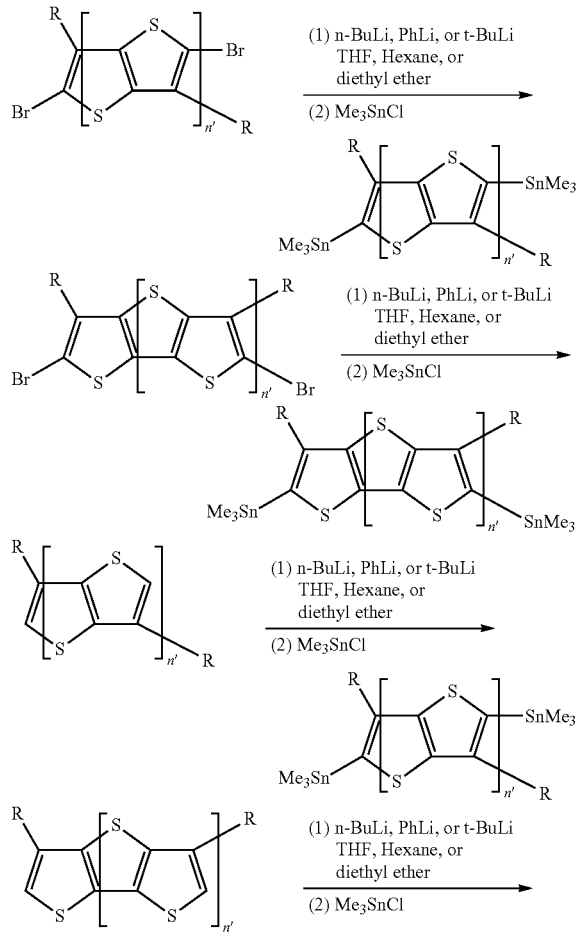

Scheme 6.

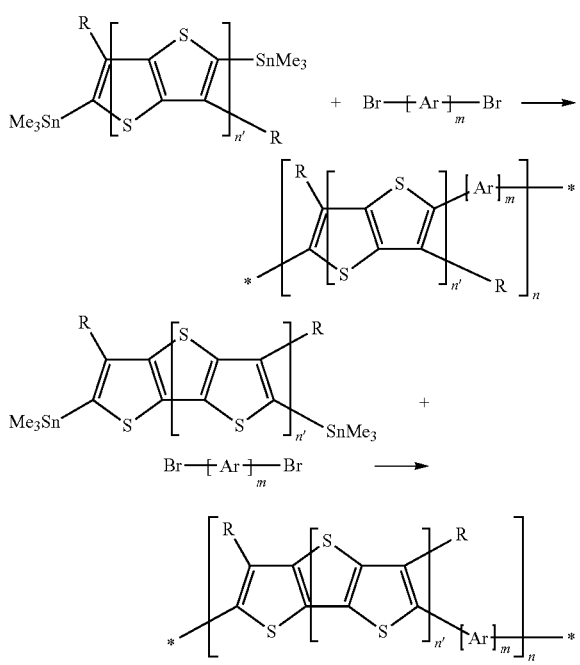

Scheme 7 shows routes for preparing β-, β'-alkyl substituted fused thiophene compounds comprising coupled products having FTx cores having appended aromatic substituents $G_1$ prepared by reacting a fused thiophene di-tin compound with at least two equivalents of a non-fused aromatic monobromo compound $G_1$-Br where n' is an integer of 1, 2, or 3, and -$G_1$ is a monovalent substituent selected from a five or six-membered aromatic, fused aromatic, vinyl substituent, acetylene substituent, or like substituents, including substituted and unsubstituted like substituents.

Scheme 7.

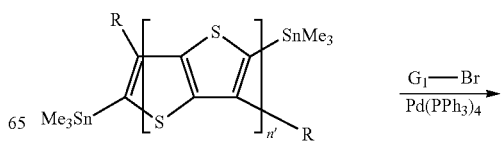

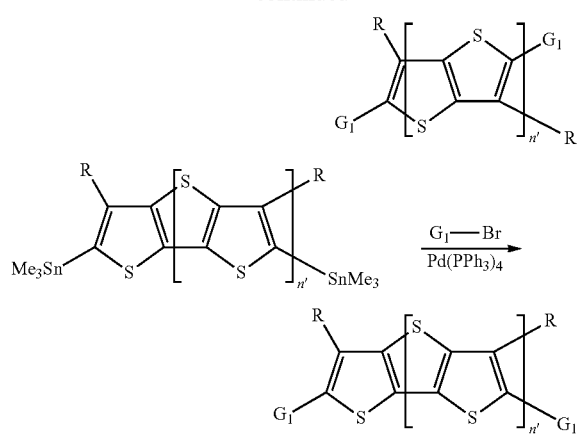

Scheme 8 shows syntheses of exemplary reactant di-tin monomer compounds 6 (FT2) and 8 (FT4), and di-bromo monomer compound 3.

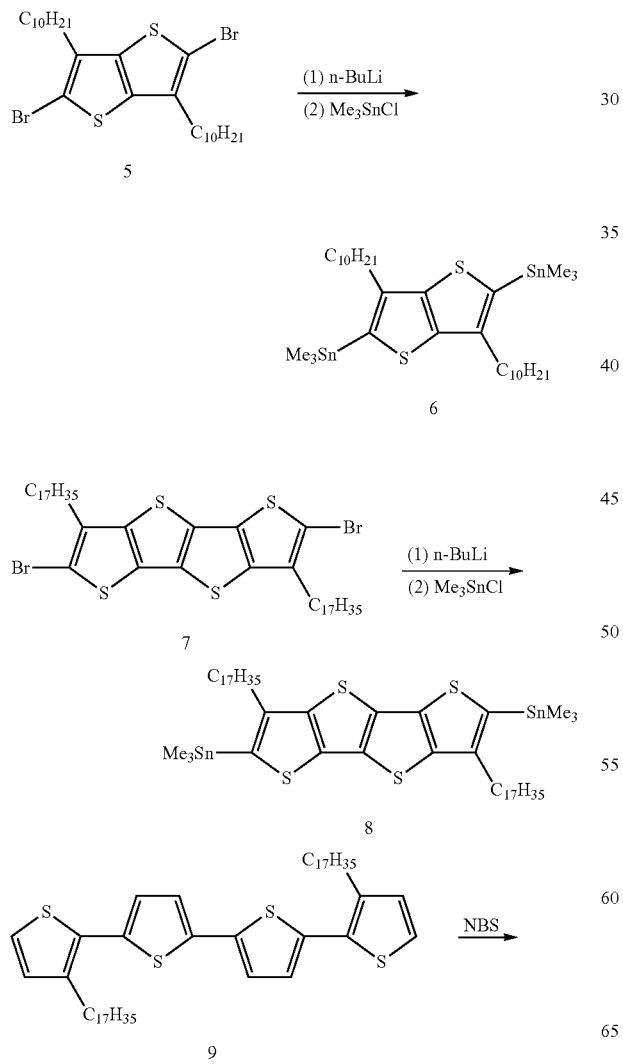

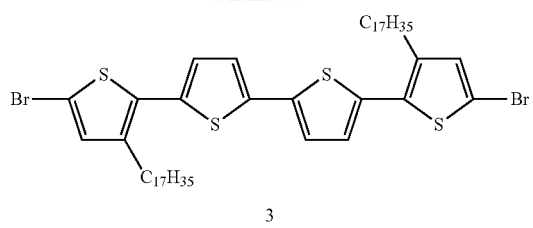

Scheme 9 shows an example of further elaboration of a FT4 reactant, i.e., an α, α'-thiophene, β-, β'-alkyl substituted fused thiophene compound 10 prepared by reacting a fused thiophene di-tin monomer 2 with at least two equivalents of 2-bromo thiophene, or like reactants, and a suitable metal catalyst.

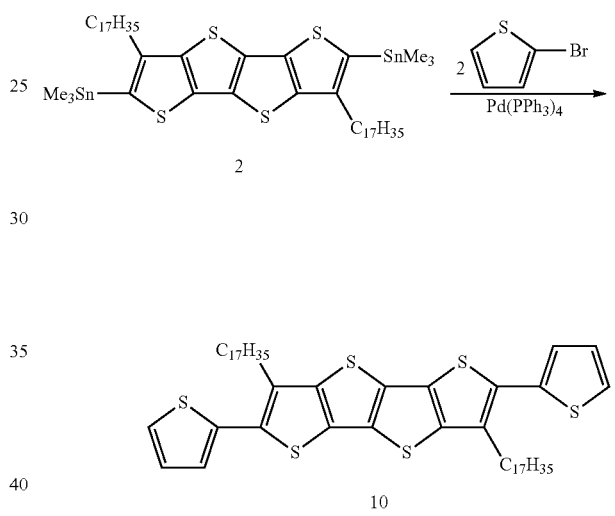

Scheme 10 shows an example of a β-, β'-alkyl substituted fused thiophene polymer 11 prepared by reacting di-tin di-alkyl substituted FT2 fused thiophene monomer compound 6 with a dibromo di-alkyl substituted FT4 fused thiophene monomer compound 7 and a suitable metal catalyst.

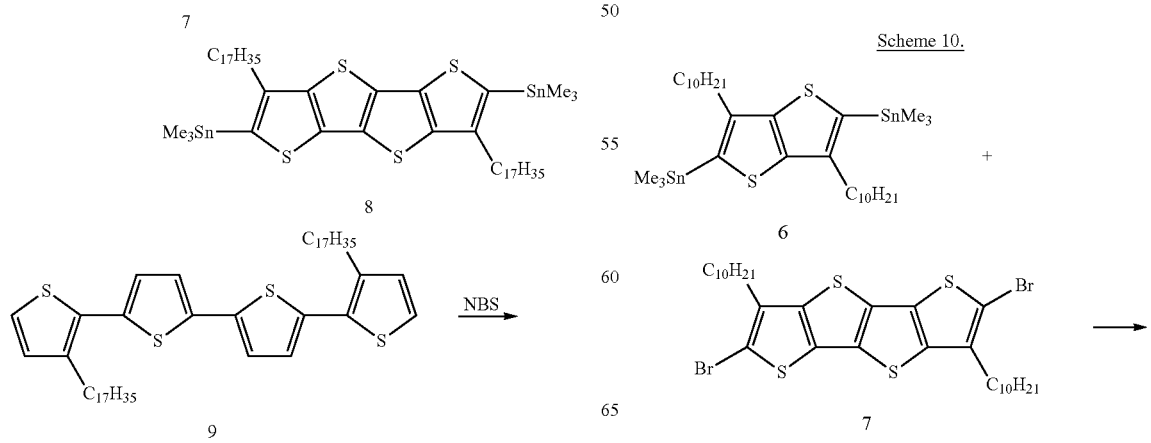

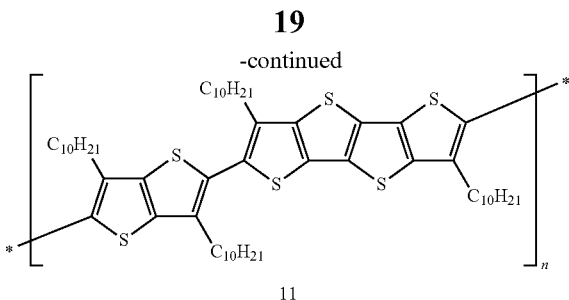

11

The disclosure provides methods of making β-, β'-alkyl substituted fused thiophene di-tin monomer materials. As shown in Scheme 5, these fused thiophene di-tin monomer compounds can be synthesized by using either a parent fused thiophene or a dibromo (halogenated) fused thiophene as the reactant. Extensive experimental research was conducted to determine various routes for preparing di-tin fused thiophene monomer compounds. Two compounds, di-tin compound 6 (abbreviated as Ditin DC10FT2) (Scheme 8) and di-tin compound 8 (Ditin DC17FT4) (Scheme 8) were prepared using dibromo precursors. Compound 6 (Ditin DC10FT2) was prepared using compound 5 (DiBr DC10FT2) as a reactant. The dibromo compound can be prepared using any suitable halogenating agent, for example, a brominating agent, such as NBS, $Br_2$, a chlorinating agent such as NCS, $Cl_2$, an iodinating agent such as NIS, $I_2$, and like agents, or combinations thereof. Although not wanting to be limited by theory, a reaction temperature of −78° C. with n-BuLi was suitable for the di-Br compound 5 to form a dianion which reacted with $Me_3SnCl$ to form di-tin compound 6. The di-tin compound 6 was used for polymerization without any further purification. The same reaction condition was successfully applied in the polymer synthesis reported (Lee, J-Y, et al., *J. Materials Chem.* (2009), supra.) using the DC15FT2 di-tin compound (Scheme 4). However, attempted synthesis of di-tin compound 8 (Ditin DC17FT4) (Scheme 8) using compound 7 (DiBr DC17FT4) as the reactant under this reaction condition only provided recovered reactant compound 7 (Table 1). Although not limited by theory this may be due to the limited solubility of the reactant compound 7 (DiBr DC17FT4) or its salt(s) in THF at low temperature. The reaction temperature of n-BuLi with compound 7 in THF was then raised to room temperature (Table 1), and produced a complex mixture after the addition of $Me_3SnCl$ and work-up. The desired di-tin compound 8 (Ditin DC17FT4) could not be detected by $^1$H NMR in the complex mixture. It was found that the reaction of n-BuLi with compound 7 in refluxing hexane experiment (Table 1), produced the desired di-tin compound 8 (Ditin DC17FT4) as the major product after the addition of $Me_3SnCl$ and work-up. Both di-tin compound 6 and di-tin compound 8 were purified and characterized by $^1$H NMR.

In embodiments, the disclosure also provides an alternative method to prepare conjugated copolymers of β-, β'-alkyl substituted fused thiophenes. Such fused thiophene copolymers can be prepared by, for example, a Stille coupling between a di-tin fused thiophene monomer compound and a dibromo aromatic monomer compound, a dibromo heteroaromatic monomer compound, a dihalo-vinyl monomer compound, or like compound combinations. Two experimental points of interest of using this chemistry to prepare fused thiophene polymer 4 are illustrated in Scheme 3. The formation of a pure polymer 4, having repeat units with $C_2$ symmetry and improved solubility, is supported by its $^1$H NMR and UV-Vis spectra. An interesting property of this polymer is that the maximum peak in its solid UV-Vis spectrum has about a 55 nm red-shift compared to the maximum peak in its solution UV-Vis spectrum in $CHCl_3$. This indicates a good pi-stack in the solid state, which can be a significant property for polymers as organic thin film transistors. OTFT device data of polymer 4 having improved solubility has a mobility of about 0.0155 $cm^2V^{-1}s^{-1}$ and an on/off ratio of $10^5$ (Table 3).

Ong has been active in the area of polymeric fused thiophenes but has not mentioned a polymer having the general structure of 4 including a 3,3'-dialkyl quaterthiophene unit (see Ong, B. S., et al., Eur. Pat. Appl. (2003), 42 p. EP 1327647).

Polymer 4 had superior solubility compared to a published high performance organic semiconducting polymer (see Fong, H. H., et al., supra.). For example, polymer 4 is soluble in heated hexane and toluene. For the small molecule synthesis using the alternative preparative method, the general chemistry shown in Scheme 7 was supported by the specific reaction of Scheme 9.

EXAMPLES

The following examples serve to more fully describe the manner of using the above-described disclosure, and the best modes contemplated for carrying out various aspects of the disclosure. It is understood that these examples do not limit the scope of this disclosure, but rather are presented for illustrative purposes.

Example 1

3,6-Bis(decyl)-5-(trimethylstannyl)thieno[3,2-b] thiophen-2-yl-trimethylstannane; Di-tin FT2 compound 6 (DiSnDC10FT2) (Scheme 8) To compound 5 (3.04 g, 5.25 mmol) in 50 mL THF at −78° C., was added dropwise n-BuLi (2.5 M in hexane) (4.2 mL, 10.5 mmol). The resulting solution was stirred at −78° C. for 4 h. Next a $Me_3SnCl$ solution (1 M in THF) (20.0 mL, 20 mmol) was added dropwise. The cloudy mixture was warmed to room temperature and stirred overnight. 100 mL of water was added into the cloudy mixture and the THF was removed with reduced pressure to yield a cloudy aqueous residue. This residue was dissolved in ethyl acetate and washed with water and then dried over $MgSO_4$ (anhydrous). After solvent evaporation, the residue was recrystallized from EtOH at −78° C. to form the desired product 6 as a waxy solid in about 85% purity (1.84 g, 47%). $^1$H NMR (300 MHz, $CD_2Cl_2$): δ 2.68 (t, J=7.0 Hz, 4H), 1.65 (p, J=7.3 Hz, 4H), 1.45-1.13 (m, 32 H), 0.88 (t, J=7.1 Hz, 6H), 0.39 (s, 18H).

Example 2

Di-tin FT4 compound 8 (DiSnDC17FT4) (Scheme 8) To compound 7 (2.67 g, 3.01 mmol) in 300 mL hexane at −78° C. was added dropwise n-BuLi (4.29 mL, 12.87 mmol) (2.0 M in hexane). The resulting solution was warmed to rt and then refluxed for 4 h. A $Me_3SnCl$ solution (1 M in THF) (9.0 mL, 9.0 mmol) was added dropwise at room temperature to the reaction. The cloudy reaction solution was stirred overnight. 100 mL of water was added to the cloudy solution and THF was removed with reduced pressure to yield a cloudy aqueous residue. This residue was dissolved in ethyl acetate and washed with water, and then dried over $MgSO_4$ (anhydrous). After the evaporation of solvent, the resulting residue was recrystallized from diethyl ether to provide the di-tin compound 8 as an off-white solid (2.51 g, 79%). Mp. 53-55° C. $^1$H NMR (300 MHz, CD$_2$Cl$_2$): δ 2.75 (t, J=7.8 Hz, 4 μl), 1.74 (p, J=7.0 Hz, 4H), 1.47-1.17 (m, 56H), 0.88 (t, J=7.1 Hz, 6H), 0.44 (s, 18H).

Table 1 provides a listing of some experimental conditions that were explored for the reaction of compound 7 (DiBr-DC17FT4) or the non-halogenated equivalent (DC17FT4) compound (not shown) and n-BuLi, to prepare di-tin compound 8 (Di-tin DC17FT4) shown in Scheme 8.

TABLE 1

| Reactant | Solvent | Reaction temperature ° C. (time) | Di-tin compound 8 formed? | Reactant compound 7 recovered? | Isolated and Purified yield |
| --- | --- | --- | --- | --- | --- |
| DiBr-DC17FT4 | THF | −78° C. (8 hrs) then warmed to −20° C. | None | Yes | 0% |
| DiBr-DC17FT4 | THF | −78° C. then warmed to 0° C. | None | Yes | 0% |
| DiBr-DC17FT4 | THF | −78° C. (8 hrs) then warmed to rt | complex mixture | Yes | complex mixture |
| DiBr-DC17FT4 | diethyl ether | refluxed 10 hrs | None | Yes | 0% |
| DC17FT4 | THF | −78° C. (2 hrs) then warmed to −20° C. | None | Yes | 0% |
| DiBr-DC17FT4 | hexane | refluxed for 4 hrs | Yes | No | 79% |

Table 2 provides solubility properties and a solubility comparison of di-Br compound 7 and di-tin compound 8. The comparison made it readily apparent that the solubility properties of the di-Br compound 7 are significantly different compared to the di-tin compound 8. The di-Br compound 7 was essentially insoluble or only partially soluble in direct comparisons to compound 8.

TABLE 2

| FT4 Compound | Solvent Volume (mL) | hexane | toluene | CH$_2$Cl$_2$ |
| --- | --- | --- | --- | --- |
| Di-Br DC17FT4 | 5 | − | − | − |
| (10 mg) (compound 7) | 10 | − | − | − |
|  | 15 | − | 0 | − |
|  | 20 | − | 0 | 0 |
| Di-tin DC17FT4 | 5 | ++ | ++ | ++ |
| (30 mg) (compound 8) | 10 | ++ | ++ | ++ |
|  | 15 | ++ | ++ | ++ |
|  | 20 | ++ | ++ | ++ |

Key:
− = insoluble
0 = partially soluble
+ = nearly all soluble; some minor residual
++ = complete solubility Example 3

Dibromo dialkyl substituted quaterthiophene compound 3 (Scheme 8) To a stirred solution of compound 9 (1.48 g, 1.83 mmol) in dichloromethane (DCM) (10 mL) at 0° C., a solution of N-bromosuccinimide (NBS) (0.69 g, 3.85 mmol) in DMF (15 mL) was added dropwise. The resulting mixture was stirred in darkness for 16 hours. Then 60 mL of water was added to this solution and DCM was removed. An additional 500 mL of water was added into the resulting DMF solution. The light yellow precipitate that formed was collected and washed with water and MeOH. It was recrystallized from hexane to yield compound 3 as a light yellow powder (1.31 g, 74% yield). $^1$H NMR (300 MHz, CD$_2$Cl$_2$): δ 7.14 (d, J=3.9 Hz, 2H), 6.99 (d, J=3.9 Hz, 2H), 6.93 (s, 2H), 2.73 (t, J=7.5 Hz, 4H), 1.62 (t, J=7.5 Hz, 4H), 1.42-1.18 (m, 56H), 0.88 (t, J=6.6 Hz, 6H).

Example 4

Synthesis of small model compound 10 (Scheme 9) To 0.34 g of compound 2 (1.84 mmol) in a microwave reaction test tube fitted with a stir bar was added 0.11 g (0.677 mmol) of 2-bromo thiophene. The tube was flushed with nitrogen for several minutes. After the tube was sealed the test tube was placed in a glove box, and 0.015 g (0.0129 mmol) of Pd(PPh$_3$)$_4$ and 10 mL of toluene were added to the tube. The tube was sealed and seated into the microwave reactor. After 40 minutes at 120° C. in the microwave reactor the reaction mixture was purified by column chromatography (hexane as the eluent). The desired product 10 was collected as a light yellow solid after removal of hexane solvent (0.11 g, 38% yield). The $^1$H NMR matched that previously reported (see commonly owned and assigned copending patent application U.S. Ser. No. 12/473,652 to He, et al., (supra.)).

Example 5

Polymer 11 (Scheme 10) Di-tin compound 6 (1.02 g, 1.36 mmol) and di-bromo fused thiophene (diBrDC17FT4) compound 7 (0.94 g, 1.36 mmol) were placed in a three neck flask fitted with a stir bar then purged with nitrogen for several minutes. After the flask was sealed it was placed in a glove box. 0.078 g (0.068 mmol) of Pd(PPh$_3$)$_4$ and 30 mL of chlorobenzene were added to the flask. The mixture was heated to about 120° C. under nitrogen for 16 h before being cooled and poured into a solution of methanol (200 mL) and concentrated hydrochloric acid (5 mL). The mixture was stirred overnight at room temperature. The precipitate was filtered and Soxhlet extracted, first with acetone for 24 h and then hexane for 2 h. The collected polymer was dried in vacuum to provide 1.09 grams of polymer 11 as a yellow solid in a yield of 84%. The number of repeat units (n) of the coupled dialkyl substituted FT2 and dialkyl substituted FT4 was about 10.

Example 6

FT4 copolymer 4 (Scheme 3) Di-tin compound 2 (443.0 mg, 0.420 mmol) and diBr compound 3 (405.3 mg, 0.420 mmol) were placed in a three neck flask fitted with a stir bar and purged with nitrogen for several minutes. After the flask was sealed it was placed in a glove box. In the glove box, 24.3 mg (0.068 mmol) of Pd(PPh$_3$)$_4$ and 20 mL of toluene were added to this flask. The resulting mixture was heated to about 120° C. under nitrogen overnight then poured into a solution of methanol (250 mL) and concentrated hydrochloric acid (3 mL). The quenched mixture was stirred overnight at room temperature. The resulting precipitate was filtered and Soxhlet extracted with acetone for 24 h. The collected polymer was vacuum dried to yield 0.62 grams of dark-red solid as polymer 4 in a yield of 81%. ($\lambda_{max}$ in CHCl$_3$ solution=459 nm, $\lambda_{max}$ in thin film=514 nm). $^1$H NMR (300 MHz, CD$_2$Cl$_2$): δ 7.21-6.92 (br m, 6H), 3.17-2.62 (br m, 8H), 1.90-1.15 (br m, 120H), 0.95-0.78 (br m, 12H).

Example 7

FT4 Copolymer 4 Device Fabrication and Characterization
All top-contact bottom-gate transistors using polymer 4 as an organic semiconducting channel were fabricated in air. Si<100> wafers were used as gate electrodes with silicon dioxide as the gate dielectric. OFET devices based on polymer 4 were fabricated on the C8OTS vapor treated Si/SiO$_2$ wafers. Polymer films were annealed at 150° C. Device testing results are shown in Table 3.

TABLE 3

Device Fabrication and Testing Results for FT4 Copolymer 4.
Solvent: toluene

| Device | mobility | Vt | On/Off | Device | mobility | Vt | On/Off |
|---|---|---|---|---|---|---|---|
| Substrate 1 | | | | Substrate 2 | | | |
| Average | 5.05E−03 | 19.08 | ~10$^4$ | Average | 6.23E−03 | 4.27 | ~10$^4$ |
| s.d. | 6.02E−04 | 14.25 | — | s.d. | 7.35E−04 | 4.56 | — |
| Min | 4.12E−03 | 0.71 | | Min | 4.96E−03 | −1.62 | |
| Max | 6.60E−03 | 40.65 | | Max | 7.61E−03 | 18.96 | |
| Solvent: dichlorobenzene | | | | Solvent: pentachloroethane | | | |
| Average | 1.55E−02 | 2.90 | ~10$^5$ | Average | 1.83E−02 | 3.18 | ~10$^5$ |
| s.d. | 2.84E−03 | 2.06 | — | s.d. | 4.22E−03 | 3.25 | — |
| Min | 9.19E−03 | −0.84 | | Min | 1.10E−02 | −1.28 | |
| Max | 2.24E−02 | 6.49 | | Max | 2.67E−02 | 12.86 | |

Example 8

Prophetic

FT6 copolymer Example 6 can be repeated with the exception that the di-tin FT4 compound 2 is replaced with the corresponding di-tin FT6 compound. The corresponding di-tin FT6 compound can be prepared using the procedures used to prepare the di-tin FT4 compound 2.

The disclosure has been described with reference to various specific embodiments and techniques. However, it should be understood that many variations and modifications are possible while remaining within the spirit and scope of the disclosure.

What is claimed is:

1. A compound of the formula (I) or (II):

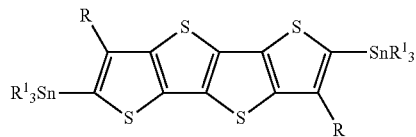
(I)

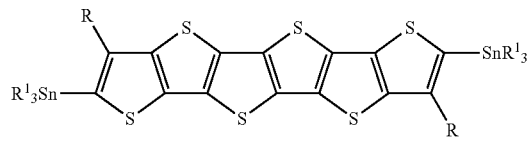
(II)

where
each R is independently —H, or a substituted or unsubstituted, (C$_{1-24}$)hydrocarbyl;
each R$^1$ is independently —H, or a substituted or unsubstituted, (C$_{1-10}$)hydrocarbyl;
or a combination thereof, and a salt thereof.

2. The compound of claim 1 wherein R is a C$_{10}$ to C$_{18}$ alkyl, and R$^1$ is a C$_1$ to C$_6$ alkyl.

3. The compound of claim 1 wherein R is C$_{17}$H$_{35}$ and R$^1$ is CH$_3$.

4. The compound of claim 3 wherein the di-tin compound R$^1_3$Sn-DC17FT4-SnR$^1_3$ of the formula (I) has excellent solubility in hexane, toluene, CH$_2$Cl$_2$, or mixtures thereof, compared to the corresponding di-bromo compound Br-DC17FT4-Br.

5. A polymer of the formula (11):

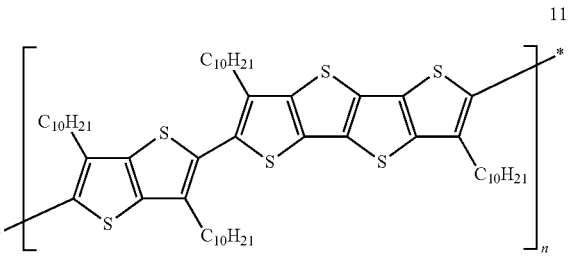
11 where n is an integer of 5 to 20, and salts thereof.

6. The polymer of claim 5 wherein n is 10.

7. A method of making a polymer of formula (III) or (IV):

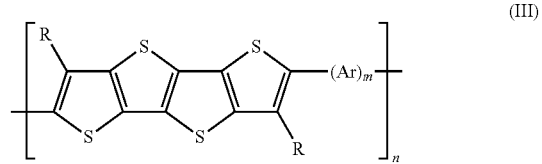
(III)

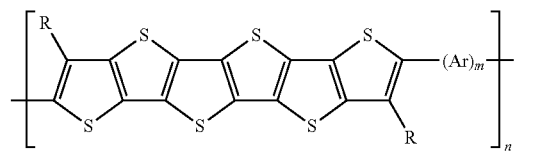
(IV)

comprising:
    contacting a dihalogen compound of formula (V) or (VI)

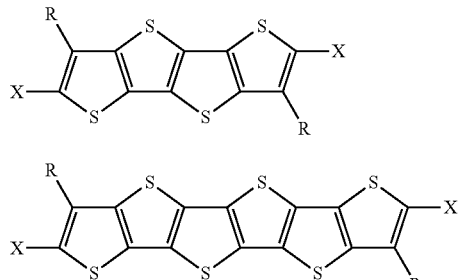

and at least two equivalents of an alkyl lithium reagent or an aryl lithium reagent to form the metal-halogen exchange intermediate, and then contacting the intermediate with a trialkylene tin halide compound to form the di-tin compound of formula (I) or (II) of claim 1:

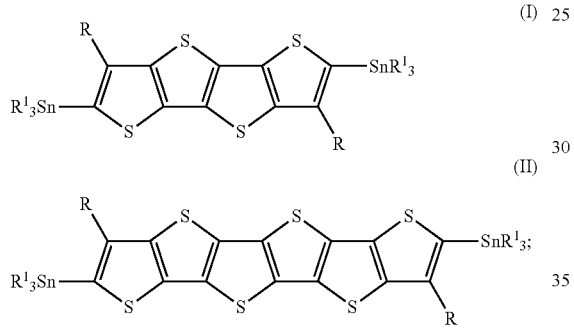

and contacting the compound of formula (I) or (II) with a dihalogen aryl compound or dihalogen heteroaryl compound of the formula X-(Ar)$_m$—X, and a metal catalyst to form the polymer of the formula (III) or (IV),
where
    m and n, are independently integers from 1 to 20,
    each R is independently —H, or a substituted or unsubstituted, (C$_{1-24}$)hydrocarbyl;
    each R$^1$ is independently —H, or a substituted or unsubstituted, (C$_{1-10}$)hydrocarbyl;
    each Ar is independently a substituted or unsubstituted divalent aryl or heteroaryl, and
    X is halogen, and a salt thereof.

8. The method of claim 7 wherein the dihalogen aryl compound or dihalogen heteroaryl compound of the formula X-(Ar)$_m$—X is Br-(thiophene)$_m$-Br and m is 2 to 4.

9. The method of claim 7 wherein the dihalogen aryl compound or dihalogen heteroaryl compound of the formula X-(Ar)$_m$—X is a Br-{(thiophene)$_a$(beta-alkyl-substituted-thiophene)$_b$}-Br where the beta-alkyl-substituent R is —C$_{17}$H$_{35}$, a is 2, b is 2, and m is 4.

10. The method of claim 7 wherein the dihalogen aryl compound or dihalogen heteroaryl compound of the formula X-(Ar)$_m$—X is:
    Br-{(beta-C$_{17}$-substituted-thiophene)(thiophene)$_2$ (beta-C$_{17}$-substituted-thiophene)}-Br.

11. The method of claim 7 wherein the alkyl lithium reagent or an aryl lithium reagent is selected from n-butyl lithium, t-butyl lithium, phenyl lithium, or a combination thereof.

12. The method of claim 7 wherein the metal-halogen exchange is accomplished in refluxing hexane and the alkyl lithium reagent is n-butyl lithium.

13. A device comprising at least one polymer of the formula (III), (IV):

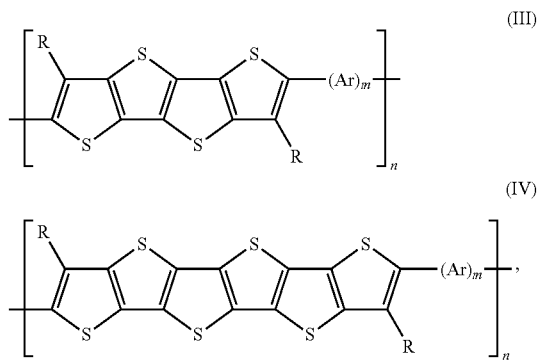

where
    m and n, are independently integers from 1 to 20,
    each R is independently —H, or a substituted or unsubstituted, (C$_{1-24}$)hydrocarbyl; and
    each Ar is independently a substituted or unsubstituted divalent aryl or heteroaryl,
and a salt thereof, or a mixture thereof.

14. The device of claim 13 wherein the polymer is of the formula (III) where R is C$_{17}$H$_{35}$, Ar is -{(beta-C$_{17}$-substituted-thiophene) (thiophene)$_2$ (beta-C$_{17}$-substituted-thiophene)}-, m is 4, and n is 5 to 20.

15. The device of claim 14 wherein the polymer has a mobility of about 0.005 to about 0.05 cm$^2$V$^{-1}$s$^{-1}$ and the on/off ratio is about 10$^5$.

16. The device of claim 14 wherein the polymer has a mobility of about 0.0155 cm$^2$V$^{-1}$s$^{-1}$.

* * * * *